United States Patent
Dinger et al.

(10) Patent No.: US 11,096,738 B2
(45) Date of Patent: Aug. 24, 2021

(54) TREATMENT OF SPINAL TISSUE

(71) Applicant: Aerin Medical, Inc., Sunnyvale, CA (US)

(72) Inventors: Fred Dinger, Austin, TX (US); Andrew Frazier, Sunnyvale, CA (US)

(73) Assignee: Aerin Medical, Inc., Sunnyvale, CA (US)

( * ) Notice: Subject to any disclaimer, the term of this patent is extended or adjusted under 35 U.S.C. 154(b) by 738 days.

(21) Appl. No.: 15/955,815

(22) Filed: Apr. 18, 2018

(65) Prior Publication Data

US 2018/0317997 A1    Nov. 8, 2018

Related U.S. Application Data

(60) Provisional application No. 62/501,895, filed on May 5, 2017.

(51) Int. Cl.
*A61B 18/14* (2006.01)
*A61N 1/36* (2006.01)
(Continued)

(52) U.S. Cl.
CPC ............ *A61B 18/14* (2013.01); *A61B 18/148* (2013.01); *A61B 18/1442* (2013.01); *A61N 1/36062* (2017.08); *A61B 2018/0016* (2013.01); *A61B 2018/0072* (2013.01); *A61B 2018/00339* (2013.01); *A61B 2018/00702* (2013.01); *A61B 2018/00755* (2013.01); *A61B 2018/00791* (2013.01); *A61B 2018/00797* (2013.01); *A61B 2018/00875* (2013.01); *A61B 2018/124* (2013.01); *A61B 2018/1405* (2013.01)

(58) Field of Classification Search
CPC ... A61B 18/14; A61B 18/1442; A61B 18/148; A61B 2018/0016; A61B 2018/00339; A61B 2018/00702; A61B 2018/0072; A61B 2018/00755; A61B 2018/00791; A61B 2018/00797; A61B 2018/00875; A61B 2018/124; A61B 2018/1405
See application file for complete search history.

(56) References Cited

U.S. PATENT DOCUMENTS

| | | |
|---|---|---|
| 4,887,605 A | 12/1989 | Angelsen et al. |
| 5,348,008 A | 9/1994 | Bomn et al. |

(Continued)

FOREIGN PATENT DOCUMENTS

| | | |
|---|---|---|
| CN | 101325919 | 12/2008 |
| WO | 199907299 | 2/1999 |

(Continued)

*Primary Examiner* — Michael F Peffley
(74) *Attorney, Agent, or Firm* — Merchant & Gould P.C.

(57) ABSTRACT

A method of treating an intervertebral disc without piercing the disc involves navigating a treatment element to the intervertebral disc and contacting the treatment element with an exterior of the intervertebral disc. The method further involves applying an energy-based treatment to the exterior of the intervertebral disc to modify a property of a target tissue of the intervertebral disc. The target tissue may be, for example, annulus fibrosus and/or nucleus pulposus tissue. The treatment element is then removed, and the property remains modified after the treatment element is removed and the target tissue heals, thereby treating the intervertebral disc.

9 Claims, 9 Drawing Sheets

(51) Int. Cl.
  *A61B 18/00* (2006.01)
  *A61B 18/12* (2006.01)

(56) References Cited

U.S. PATENT DOCUMENTS

| | | | |
|---|---|---|---|
| 5,533,499 A | 7/1996 | Johnson |
| 5,542,916 A | 8/1996 | Hirsch et al. |
| 5,624,439 A | 4/1997 | Edwards et al. |
| 5,674,191 A | 10/1997 | Edwards et al. |
| 5,707,349 A | 1/1998 | Edwards |
| 5,718,702 A | 2/1998 | Edwards |
| 5,728,094 A | 3/1998 | Edwards |
| 5,730,719 A | 3/1998 | Edwards |
| 5,733,280 A | 3/1998 | Avitall |
| 5,738,114 A | 4/1998 | Edwards |
| 5,743,870 A | 4/1998 | Edwards |
| 5,743,904 A | 4/1998 | Edwards |
| 5,746,224 A | 5/1998 | Edwards |
| 5,800,429 A | 9/1998 | Edwards |
| 5,807,306 A | 9/1998 | Shapland et al. |
| 5,816,095 A | 10/1998 | Nordell, II et al. |
| 5,817,049 A | 10/1998 | Edwards |
| 5,820,580 A | 10/1998 | Edwards et al. |
| 5,823,197 A | 10/1998 | Edwards |
| 5,827,277 A | 10/1998 | Edwards |
| 5,843,021 A | 12/1998 | Edwards et al. |
| 5,843,077 A | 12/1998 | Edwards |
| 5,846,235 A | 12/1998 | Pasricha et al. |
| 5,879,349 A | 3/1999 | Edwards |
| 5,938,659 A | 8/1999 | Tu |
| 6,045,549 A | 4/2000 | Smethers et al. |
| 6,096,033 A | 8/2000 | Tu et al. |
| 6,102,907 A | 8/2000 | Smethers et al. |
| 6,109,268 A | 8/2000 | Thapliyal et al. |
| 6,126,657 A | 10/2000 | Edwards et al. |
| 6,131,579 A | 10/2000 | Thorson et al. |
| 6,139,546 A | 10/2000 | Koenig et al. |
| 6,152,143 A | 11/2000 | Edwards |
| 6,165,173 A | 12/2000 | Kamdar et al. |
| 6,179,803 B1 | 1/2001 | Edwards et al. |
| 6,210,355 B1 | 4/2001 | Edwards et al. |
| 6,228,079 B1 | 5/2001 | Koenig |
| 6,231,569 B1 | 5/2001 | Bek et al. |
| 6,293,941 B1 | 9/2001 | Strul et al. |
| 6,309,386 B1 | 10/2001 | Bek |
| 6,371,926 B1 | 4/2002 | Thorson et al. |
| 6,383,181 B1 | 5/2002 | Johnston et al. |
| 6,391,028 B1 | 5/2002 | Fanton et al. |
| 6,416,491 B1 | 7/2002 | Edwards et al. |
| 6,425,151 B2 | 7/2002 | Barnett |
| 6,431,174 B1 | 8/2002 | Knudson et al. |
| 6,451,013 B1 | 9/2002 | Bays et al. |
| 6,468,274 B1 * | 10/2002 | Alleyne ............ A61B 18/1402 606/41 |
| 6,502,574 B2 | 1/2003 | Stevens |
| 6,540,741 B1 * | 4/2003 | Underwood ......... A61B 18/149 606/32 |
| 6,551,310 B1 | 4/2003 | Ganz et al. |
| 6,562,036 B1 | 5/2003 | Ellman et al. |
| 6,575,969 B1 | 6/2003 | Rittman et al. |
| 6,589,235 B2 | 7/2003 | Wong et al. |
| 6,659,106 B1 | 12/2003 | Hovda et al. |
| 6,689,125 B1 * | 2/2004 | Keith ................ A61B 17/0401 606/32 |
| 6,911,027 B1 | 6/2005 | Edwards et al. |
| 6,978,781 B1 | 12/2005 | Jordan |
| 7,055,523 B1 | 6/2006 | Brown |
| 7,097,641 B1 | 8/2006 | Arless et al. |
| 7,114,495 B2 | 10/2006 | Lockwood, Jr. |
| 7,322,993 B2 | 1/2008 | Metzger et al. |
| 7,416,550 B2 | 8/2008 | Protsenko et al. |
| 7,442,191 B2 | 10/2008 | Hovda et al. |
| 7,655,243 B2 | 2/2010 | Deem et al. |
| 7,678,069 B1 | 3/2010 | Baker et al. |
| 7,780,730 B2 | 8/2010 | Saidi |
| 7,824,394 B2 | 11/2010 | Manstein |
| 7,850,683 B2 | 12/2010 | Elkins et al. |
| 8,128,617 B2 | 3/2012 | Bencini et al. |
| 8,137,345 B2 | 3/2012 | McNall, III et al. |
| 8,317,781 B2 | 11/2012 | Owens et al. |
| 8,317,782 B1 | 11/2012 | Ellman et al. |
| 8,936,594 B2 | 1/2015 | Wolf et al. |
| 8,986,301 B2 | 3/2015 | Wolf et al. |
| 9,072,597 B2 | 7/2015 | Wolf et al. |
| 9,125,677 B2 | 9/2015 | Sobol |
| 9,179,964 B2 | 11/2015 | Wolf et al. |
| 9,179,967 B2 | 11/2015 | Wolf et al. |
| 9,237,924 B2 | 1/2016 | Wolf et al. |
| 9,452,087 B2 | 1/2016 | Holm et al. |
| 9,415,194 B2 | 8/2016 | Wolf et al. |
| 9,433,463 B2 | 9/2016 | Wolf et al. |
| 9,452,010 B2 | 9/2016 | Wolf et al. |
| 9,486,278 B2 | 11/2016 | Wolf et al. |
| 9,526,571 B2 | 12/2016 | Wolf et al. |
| 9,687,288 B2 | 6/2017 | Saadat |
| 9,687,296 B2 | 6/2017 | Wolf et al. |
| 9,763,723 B2 | 9/2017 | Saadat |
| 9,763,743 B2 | 9/2017 | Lin |
| 9,788,886 B2 | 10/2017 | Wolf et al. |
| 9,801,752 B2 | 10/2017 | Wolf et al. |
| 9,888,957 B2 | 2/2018 | Wolf et al. |
| 9,913,682 B2 | 3/2018 | Wolf et al. |
| 9,943,361 B2 | 4/2018 | Wolf et al. |
| 10,028,780 B2 | 7/2018 | Wolf et al. |
| 10,028,781 B2 | 7/2018 | Saadat |
| 2002/0016588 A1 | 2/2002 | Wong et al. |
| 2002/0049464 A1 | 4/2002 | Donofrio et al. |
| 2002/0087155 A1 | 7/2002 | Underwood et al. |
| 2002/0128641 A1 | 9/2002 | Underwood et al. |
| 2003/0144659 A1 | 7/2003 | Edwards |
| 2003/0208194 A1 | 11/2003 | Hovda et al. |
| 2003/0225403 A1 | 12/2003 | Woloszko et al. |
| 2004/0220644 A1 | 11/2004 | Shalev et al. |
| 2005/0020901 A1 | 1/2005 | Belson |
| 2005/0119643 A1 | 6/2005 | Sobol et al. |
| 2005/0222565 A1 | 10/2005 | Manstein |
| 2005/0234439 A1 | 10/2005 | Underwood |
| 2005/0240147 A1 | 10/2005 | Makower et al. |
| 2005/0288665 A1 | 12/2005 | Woloszko et al. |
| 2006/0235377 A1 | 10/2006 | Earley |
| 2006/0253117 A1 | 11/2006 | Hovda et al. |
| 2006/0276817 A1 | 12/2006 | Vassallo et al. |
| 2007/0066944 A1 | 3/2007 | Nyte |
| 2007/0073282 A1 | 3/2007 | McGarrigan et al. |
| 2007/0219600 A1 | 9/2007 | Gertner et al. |
| 2008/0027423 A1 | 1/2008 | Choi et al. |
| 2008/0027480 A1 | 1/2008 | van der Burg et al. |
| 2008/0082090 A1 | 4/2008 | Manstein |
| 2008/0125626 A1 | 5/2008 | Chang et al. |
| 2008/0312644 A1 | 12/2008 | Fourkas et al. |
| 2009/0018485 A1 | 1/2009 | Krespi et al. |
| 2009/0124958 A1 | 5/2009 | Li |
| 2009/0143821 A1 | 6/2009 | Stupak |
| 2009/0292358 A1 | 11/2009 | Saidi |
| 2010/0144996 A1 | 6/2010 | Kennedy et al. |
| 2010/0152730 A1 | 6/2010 | Makower et al. |
| 2010/0174283 A1 | 7/2010 | McNall |
| 2010/0241112 A1 | 9/2010 | Watson |
| 2011/0009737 A1 | 1/2011 | Manstein |
| 2011/0282268 A1 | 11/2011 | Baker et al. |
| 2012/0039954 A1 | 2/2012 | Cupit et al. |
| 2012/0078377 A1 | 3/2012 | Gonzales et al. |
| 2012/0172858 A1 * | 7/2012 | Harrison ................ A61B 6/12 606/33 |
| 2012/0298105 A1 | 11/2012 | Osorio |
| 2012/0316473 A1 | 12/2012 | Bonutti et al. |
| 2012/0316557 A1 | 12/2012 | Sartor et al. |
| 2012/0323227 A1 | 12/2012 | Wolf et al. |
| 2012/0323232 A1 | 12/2012 | Wolf et al. |
| 2013/0218158 A1 | 8/2013 | Danek et al. |
| 2014/0088463 A1 | 3/2014 | Wolf et al. |
| 2014/0114233 A1 | 4/2014 | Deem et al. |
| 2014/0128861 A1 * | 5/2014 | Leung ................ A61B 18/148 606/33 |

(56) References Cited

U.S. PATENT DOCUMENTS

| | | |
|---|---|---|
| 2015/0202003 A1 | 7/2015 | Wolf et al. |
| 2017/0095288 A1 | 4/2017 | Wolf et al. |
| 2017/0209199 A1 | 7/2017 | Wolf et al. |
| 2017/0231651 A1 | 8/2017 | Dinger et al. |
| 2017/0252089 A1 | 9/2017 | Hester |
| 2017/0252100 A1 | 9/2017 | Wolf et al. |
| 2017/0360495 A1 | 12/2017 | Wolf et al. |
| 2018/0000535 A1 | 1/2018 | Wolf et al. |
| 2018/0177542 A1 | 6/2018 | Wolf et al. |
| 2018/0177546 A1 | 6/2018 | Dinger et al. |
| 2018/0185085 A1 | 7/2018 | Wolf et al. |
| 2018/0228533 A1 | 8/2018 | Wolf et al. |
| 2018/0263678 A1 | 9/2018 | Saadat |
| 2018/0317997 A1 | 11/2018 | Dinger et al. |
| 2018/0344378 A1 | 12/2018 | Wolf et al. |

FOREIGN PATENT DOCUMENTS

| | | |
|---|---|---|
| WO | 2001043653 | 6/2001 |
| WO | 2003024349 | 3/2003 |
| WO | 2007037895 | 4/2007 |
| WO | 2007134005 | 11/2007 |
| WO | 2010077980 | 7/2010 |
| WO | 2012174161 | 12/2012 |
| WO | 2015047863 | 4/2015 |
| WO | 2015048806 | 4/2015 |
| WO | 2015153696 | 10/2015 |

\* cited by examiner

TREATMENT OF SPINAL TISSUE

CROSS-REFERENCE TO RELATED APPLICATIONS

This application claims the benefit of U.S. Provisional Patent Application No. 62/501,895, filed May 5, 2017, entitled, "TREATMENT OF SPINAL TISSUE." The disclosure of this priority application is hereby incorporated by reference in its entirety into the present application.

BACKGROUND

Disorders of the spine can have a particularly large effect on a patient's daily life. One type of spinal disorder occurs when the tissue of an intervertebral disc of the spine deforms out of position. In some cases, the disc's inner tissue, the nucleus pulposus, deforms out of position while remaining within the outer ring tissue of the disc, the annulus fibrosus. This condition is known as a disc protrusion or a bulging disc. In severe cases, the disc protrusion can progress to a spinal disc herniation, where the nucleus pulposus deforms out of position and escapes through a breach in the annulus fibrosus. While these conditions sometimes heal on their own, more severe instances require medical intervention. Given the importance and sensitivity of the intervertebral disc, such medical interventions can be difficult to perform and may result in further deterioration of the intervertebral disc. There exists a need in the art for improved techniques for treating intervertebral discs and other spinal tissue, while avoiding some of the disadvantages of prior techniques.

BRIEF SUMMARY

This disclosure describes devices, systems and methods for treating a vertebral column, including tissue of an intervertebral disc. For example, the devices, systems, and methods described herein may be used to reshape, remodel, strengthen, or change the properties of the tissues of the vertebral column, including but not limited to the skin, muscle, cartilage, bone, annulus fibrosus, and nucleus pulposus of, near, or associated with the vertebral column. Treatments can include modification of bulging or herniated intervertebral discs.

In one aspect of the present disclosure, a method of treating an intervertebral disc without piercing the disc involves navigating a treatment element to the intervertebral disc and contacting the treatment element with an exterior of the intervertebral disc. The method further involves applying an energy-based treatment to the exterior of the intervertebral disc to modify a property of a target tissue of the intervertebral disc. The target tissue may be, for example, annulus fibrosus and/or nucleus pulposus. After the treatment is applied, the treatment element is removed. The property remains modified after the treatment element is removed and the target tissue heals, thereby treating the intervertebral disc.

For example, the property might be a size of bulging tissue of the intervertebral disc. The method may sometimes also include measuring a temperature at or near the target tissue. The method may also further include adjusting a level of energy delivered to the target tissue, based at least in part on the measured temperature. Any suitable form of energy may be used, according to various embodiments, such as but not limited to ultrasound, microwave, heat, radio frequency, electrical, light or laser energy. Some embodiments may further involve cooling the target tissue and/or the exterior of the intervertebral disc before, during, or after delivering the radio frequency energy.

In another aspect of the present disclosure, a method of treating an intervertebral disc may involve first selecting a patient having a bulging intervertebral disc, then navigating a first treatment element to the intervertebral disc, contacting the first treatment element with a first treatment site on an exterior of the intervertebral disc, navigating a second treatment element to the intervertebral disc, and contacting the second treatment element with a second treatment site on the exterior of the intervertebral disc. Next, the method involves applying an energy-based treatment through the exterior of the intervertebral disc using the first and second treatment elements to make a modification in a target tissue, and removing the first and second treatment elements. Again, the modification in the target tissue remains at least partially after the first and second treatment elements are removed and the target tissue heals.

In some embodiments, applying the energy-based treatment involves transmitting energy from the first treatment element to the second treatment element. In some embodiments, the transmitted energy is radio frequency energy. Some embodiments further involve cooling tissue of the intervertebral disc before, during, and/or after applying the energy-based treatment. In some embodiments, the modification includes a reduction in size of target tissue of the intervertebral disc. In some embodiments, the second treatment site is a contralateral side of the intervertebral disc.

These and other aspects and embodiments are described in further detail below, in reference to the attached drawing figures.

DETAILED DESCRIPTION

Embodiments of the present application are directed to devices, systems and methods for treating tissue of the spine or vertebral column. Such embodiments may be used to treat bulging or herniated intervertebral discs. Treatment can involve lessening an interference between a disc bulge and a spinal cord, nerve roots or other structures of the spine. For example, the devices, systems, and methods described herein may be used to reshape, remodel, shrink, reduce, or otherwise modify tissue of, near, or associated with the vertebral column, including, but not limited to the skin, muscle, bone, annulus fibrosus, and nucleus pulposus.

Traditional techniques for treating an intervertebral disc include using instruments to remove nucleus pulposus from an intervertebral disc to make space for an implant or to relieve a disc herniation that is impinging the spinal cord or the spinal nerve root. These techniques involve inserting instruments into the annulus and into the disc in order to provide results. However, such techniques can damage the disc and cause disc degeneration. Disclosed techniques are relevant to overcoming some of the drawbacks of such techniques by allowing for treatment of the disc without causing deterioration of the disc, such as by treating the tissue of the disc from the exterior of the disc without needing to penetrate the disc.

According to one aspect, there is a device for treating the vertebral column. The device includes an array of non-penetrating electrodes in bipolar or monopolar (e.g., as used with a grounding pad) arrangement. The electrodes can be disposed on an instrument, such as an endoscopic probe, a flexible or rigid catheter, a clamp, or forceps. The device can include one or more handles that are rigidly or flexibly attached the proximal end of the instrument to allow proper apposition of the electrodes with the target tissue. The device can provide a conduit for radio frequency (RF) conductors to transmit RF energy from a source (e.g., generator) to the electrodes. A moveable electrode array relative to the elongate shaft and handle is also envisioned. Alternate techniques can also be used, including cryogenic surface cooling, combinations of cooling and heating technologies, and the use of cauterizing agents. In the case of RF energy, the device can apply energy to the disc, causing it to heat and subsequently shrink or shape away from nerve roots or the spinal cord. The shrinking or shaping may happen over time as a result of the patient's body's reaction to the treatment. RF energy can be controlled via temperature feedback, such as a thermocouple and RF power controller, or controlled to impart a specific total energy.

According to one aspect, a device for treating the vertebral column is provided. In one embodiment, the device has an energy-delivery element sized to be inserted at or near an intervertebral disc of the vertebral column and configured to deliver energy to or remove energy from tissues of the vertebral column.

According to one embodiment, a treatment device includes an elongate shaft having a proximal end and a distal end. The device further includes a handle at the proximal end of the elongate shaft. The device also has a treatment element at the distal end of the elongate shaft. The treatment element is sized or otherwise configured to navigate to a treatment site of the vertebral column. The treatment element is configured to apply energy to or remove energy from a treatment site.

Embodiments of treatment devices can apply various types of energy-based treatment. For example, a treatment device may apply energy in a form selected from the group consisting of ultrasound, quantum molecular resonance, microwave, heat, radio frequency, electrical, light and laser. A treatment device may remove energy from a treatment site to provide cryo or other cold therapy.

In embodiments utilizing energy-delivery (e.g., RF energy), a handle may be provided including a button or other input control to active one or more electrodes. Electrodes may include one or more monopolar plates and/or one or more bipolar electrode pairs. In some examples, when using bipolar electrode pairs, a first electrode surface may be positioned at a first location and a second electrode surface may be positioned at a second location (e.g., on an opposite side a disc) to cause energy to flow across a particular path (e.g., through a bulging portion of the disc).

The device of one energy-delivery embodiment may include an adaptor configured to be connected to an energy source, such as an RF energy source. The device may also include a control system configured to control the characteristics of energy applied to tissue. A thermocouple or other sensor may be provided to measure a temperature near tissue or measure a device parameter.

In another aspect, a system is provided including a device as described above and further below in combination with one or more other components. One such component may be an energy source, such as an RF energy source. Another component may be a control system for controlling the energy source and/or treatment device. In another embodiment, the device or system may include a cooling mechanism to cool particular tissue locations while treatment is being applied. In monopolar electrode embodiments, a grounding pad may also be provided as part of the system. Another system includes a positioning device that may be used before treatment to determine an optimal device position or other parameters for using the device.

According to another aspect, a method of treating a bulging disc is provided. In one embodiment, the method includes navigating a treatment element to an area of a bulging disc and applying treatment sufficient to modify tissue of the disc, such as the disc's annulus fibrosus or nucleus pulposus. Delivering energy may include measuring a temperature near tissue to be treated, and adjusting a level of energy delivered to the tissue.

Energy or treatment may be delivered for a sufficient period of time and in a sufficient quantity to cause a desired modification, such as shrinking of an area of tissue.

In another aspect, a method of treating a bulging disc may involve: advancing a treatment element of a treatment device into an incision in a patient to contact tissue of the vertebral column (e.g., annulus fibrosus of an intervertebral disc), delivering an energy-based therapy to the nucleus pulposus tissue through the annulus fibrosus using the treatment element, thereby reshaping, remodeling, strengthening, and/or changing a property of the nucleus pulposus or annulus fibrosus; and removing the treatment element.

Optionally, the method may further include applying force to the tissue (e.g., the annulus fibrosus) with the treatment element before, during, or after delivering the energy based therapy to modify the tissue. In some embodiments, a tissue contacting surface of the treatment element has a convex, concave, or flat shape.

In another aspect, a method of treating a patient's vertebral column may involve: adjusting a shape of a treatment device; contacting a treatment element of the treatment device tissue of an intervertebral disc; delivering an energy-based therapy to the tissue and/or an underlying tissue beneath the tissue using the treatment element; and removing the treatment element from the treatment site. Adjusting the shape may involve shaping the treatment element to have a convex treatment surface, a concave treatment surface or a flat surface, or adjusting a height of at least one electrode on a treatment surface of the treatment element. In some embodiments, adjusting the height involves adjusting multiple heights of multiple electrodes to form a treatment surface profile.

Some embodiments may involve sensing at least one temperature of at least one of the annulus fibrosus or nucleus pulposus using a sensing element on the treatment device. The delivery of the energy-based therapy may be adjusted based on the temperature. In some embodiments, sensing the temperature involves sensing multiple temperatures with multiple thermocouples located at or near multiple electrode pairs on the treatment element, where each of the multiple thermocouples is located at or near one of the multiple electrode pairs. The method may also include determining an average temperature of at least two of the multiple temperatures, wherein the delivery of the energy-based therapy is adjusted based on the average temperature. In some embodiments, adjusting the delivery may involve adjusting delivery to at least one of the electrode pairs separately from at least one other of the electrode pairs.

In another aspect, there is a method of making space for a spinal implant. The method can include applying a treatment element to tissue of an intervertebral disc. The treatment element is activated to reshape or otherwise modify the disc to create a space between vertebrae for placement of a spinal implant. In some embodiments, this can include applying pressure using the treatment element to shape, shrink, or move tissue. Following treatment, a spinal implant can be inserted into the created space. Advantageously, this approach can create space for the implant without severely compromising the disc and causing unwanted disc degradation.

In another aspect, a device for modifying at least one property of at least one tissue in a vertebral column may include: a head portion configured to pass through an incision to navigate to a region of the vertebral column; a shaft extending from the head portion; and a handle attached to the shaft at an opposite end from the head portion. The head portion may include an energy-based therapy delivery member and an incision forming member. The handle may include a housing to hold a power source for providing energy to the energy-delivery member.

In some embodiments, the energy-delivery member may include a contact surface with a convex shape configured to at least temporarily create a concavity in the at least one tissue. In some embodiments, the energy-delivery member may have a contact surface with flat shape. In some embodiments, the energy-delivery member may include multiple flexible sections configured to be manipulated. For example, the flexible sections may include multiple protruding electrodes configured to at least temporarily deform tissue. Such protruding electrodes may include two rows of electrodes, where the energy-delivery member has a bipolar radio frequency delivery member, and where radio frequency energy travels from one row of electrodes to the other row of electrodes.

In some embodiments, the housing is configured to hold at least one battery. Some embodiments may include at least one sensor configured to sense at least one of temperature or impedance in tissue of an intervertebral disc. In some embodiments, the sensor(s) may be attached to the device on or near the energy-delivery member. The device may further include a tissue cooling member attached to the device at or near the energy-delivery member.

In one embodiment, the energy-delivery member may include at least one electrode pair configured to apply energy to the at least one tissue. The device may also further include at least one thermocouple configured to sense temperature at each electrode pair. Some embodiments may further include a processor to determine an average temperature from multiple temperatures sensed by more the thermocouples. In some embodiments, each of the electrode pairs is adjustable separately from adjustment of any other of the electrode pairs.

Figure 1A:
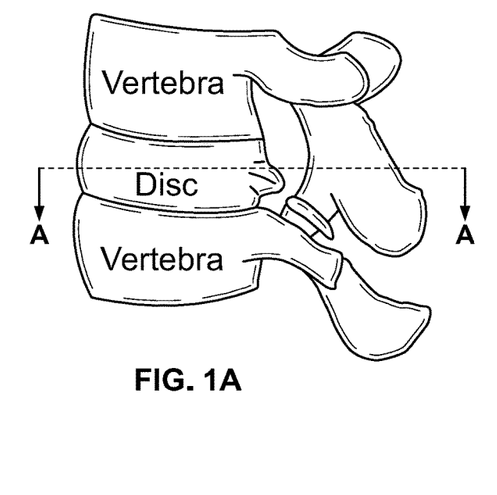
FIG. 1A illustrates an example portion of a vertebral column.

FIG. 1A illustrates an example portion of the vertebral column. The illustrated portion shows an intervertebral disc between two vertebrae. A cross-section line A-A is also shown.

Figure 1B:
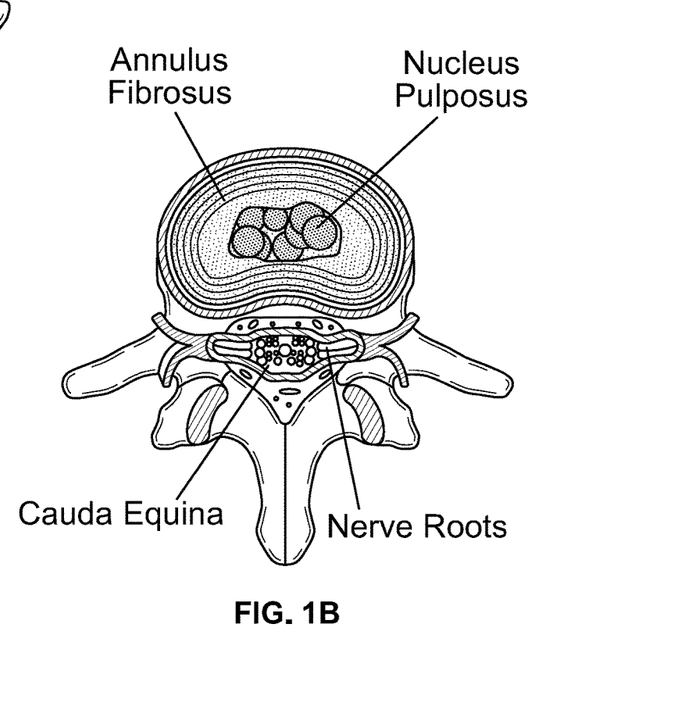
FIG. 1B illustrates an example cross-section of a typical intervertebral disc, the cross-section taken along line A-A of FIG. 1A.

FIG. 1B illustrates an example cross-section of a normal intervertebral disc taken along line A-A of FIG. 1A. The vertebral disc includes nucleus pulposus surrounded by annulus fibrosus.

Figure 1C:
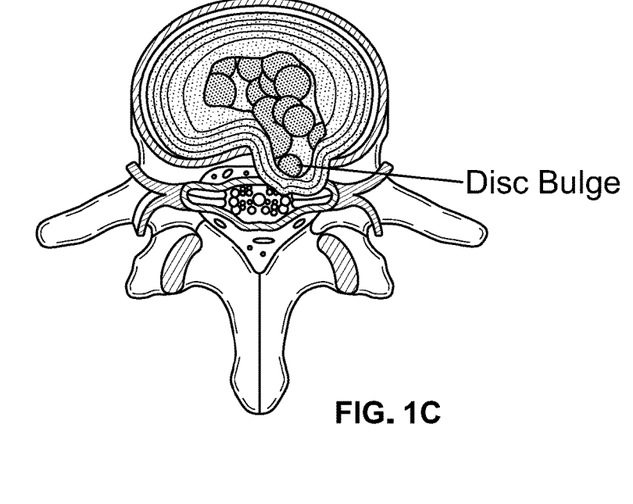
FIG. 1C illustrates an example cross-section of an intervertebral disc having a bulge, the cross section taken along line A-A of FIG. 1A.

FIG. 1C illustrates an example cross-section of an intervertebral disc having a disc bulge taken along line A-A of FIG. 1A. As illustrated, the nucleus pulposus is bulging out of its typical position and pushing a portion of the annulus fibrosus out of a typical position. In addition, this disc bulge is pushing on nerve tissue causing nerve impingement.

Figure 2:
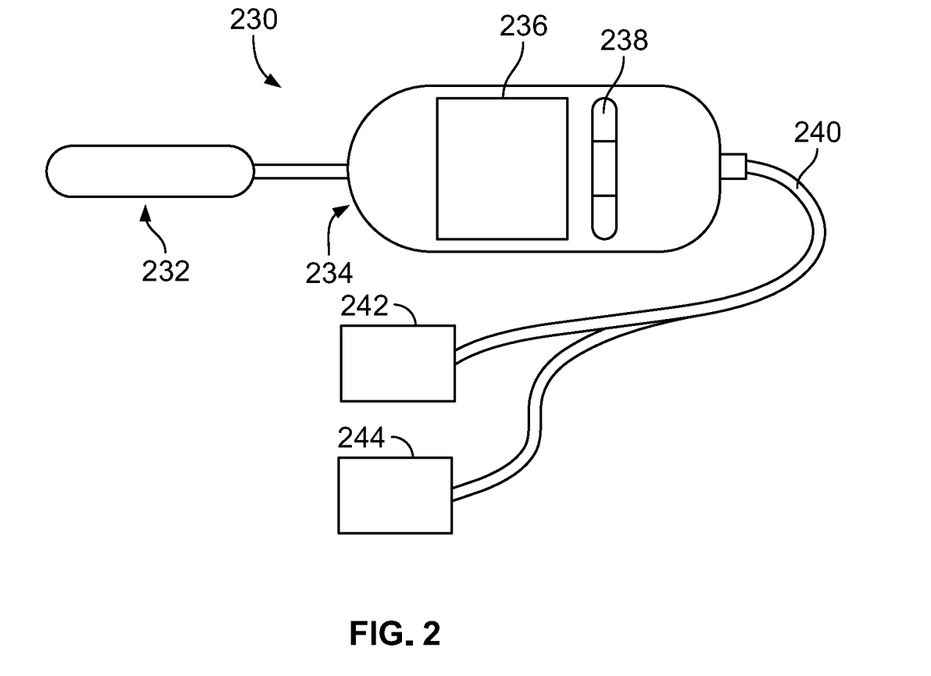
FIG. 2 illustrates an example treatment device.

FIG. 2 illustrates an example treatment device 230. The device 230 includes a treatment element 232 which may be configured to be placed in, at, or near a subject's vertebral column to deliver a desired treatment. In some embodiments, the device 230 may further include a handle section 234 which may be sized and configured for easy handheld operation by a clinician. In some embodiments, a display 236 may be provided for displaying information to a clinician during treatment.

In some embodiments, the information provided on the display 236 may include treatment delivery information (e.g. quantitative information describing the energy being delivered to the treatment element) and/or feedback information from sensors within the device and/or within the treatment element. In some embodiments, the display may provide information on physician selected parameters of treatment, including time, power level, temperature, electric impedance, electric current, depth of treatment and/or other selectable parameters.

In some embodiments, the handle section 234 may also include one or more input controls 238, such as buttons, knobs, dials, touchpads, or joysticks. In some embodiments, controls may be incorporated into the display, such as by the use of a touch screen. In further embodiments, controls may be located on an auxiliary device which may be configured to communicate with the treatment device 230 via analog or digital signals sent over a cable 240 or wirelessly, such as via BLUETOOTH, WIFI (or other 802.11 standard wireless protocol), infrared, or any other wired or wireless communication method.

In some embodiments the treatment system may include an electronic control system 242 configured to control the timing, location, intensity and/or other properties and characteristics of energy or other treatment applied to targeted regions of a vertebral column. In some embodiments, a control system 242 may be integrally incorporated into the handle section 234. Alternatively, the control system 242 may be located in an external device which may be configured to communicate with electronics within the handle section 234. The control system 242 may include a closed-loop control system having any number of sensors, such as thermocouples, electric resistance or impedance sensors, ultrasound transducers, or any other sensors configured to detect treatment variables or other control parameters.

The treatment system may also include a power supply 244. In some embodiments, the power supply 244 may be integrally incorporated within the handle section 234. In alternative embodiments, a power supply 244 may be external to the handle section 234. An external power supply 244 may be configured to deliver power to the handle section 234 and/or the treatment element 232 by a cable or other suitable connection. The power supply 244 can be configured to provide power for an energy-based treatment from the treatment element 232. In some embodiments, a power supply 244 may include a battery or other electrical energy storage or energy generation device. In other embodiments, a power supply may be configured to draw electrical power from a standard wall outlet. In some embodiments, a power supply 244 may also include a system configured for driving a specific energy-delivery technology in the treatment element 232. For example, the power supply 244 may be configured to deliver a radio frequency alternating current signal to an RF energy-delivery element. Alternatively, the power supply may be configured to deliver a signal suitable for delivering ultrasound or microwave energy via suitable transducers. In further alternative embodiments, the power supply 244 may be configured to deliver a high-temperature or low-temperature fluid (e.g. air, water, steam, saline, or other gas or liquid) to the treatment element 232 by way of a fluid conduit.

In some embodiments, the treatment element 232 may have a substantially rigid or minimally elastic form that is sized and shaped such that it substantially conforms to a shape of a portion of a vertebral column. In some embodiments, the treatment element 232 may have a curved shape, either concave or convex. In some embodiments, the shape of a fixed-shape treatment element may be substantially in a shape to be imparted to tissue-to-be-treated.

In some embodiments, the treatment element 232 and control system 242 may be configured to deliver treatment energy to create specific, localized tissue damage or ablation, which may stimulate the body's healing response to create desired conformational or structural changes in the tissue.

In some embodiments, the treatment element 232 and control system 242 may be configured to create specific localized tissue damage or ablation without the application of energy. For example the treatment element 232 may be configured to chemically cauterize or otherwise treat target tissue by delivering a chemical agent (e.g., a cauterizing agent, such as silver nitrate, trichloroacetic acid, or cantharidin) to the tissue. The treatment element 232 may include apertures configured to permit the cauterizing agent pass through to the treatment site. In some embodiments, the treatment element 232 may aerosolize the cauterizing agent. Other delivery methods are also contemplated. The treatment element 232 may include a lumen through which the cauterizing agent passes. The lumen may be fluidly connected to a reservoir or container holding the cauterizing agent. The device may include an input control (e.g., a button or switch) configured to control delivery of the cauterizing agent. In some embodiments, the treatment element 232 includes an applicator that can be coated in a cauterizing agent (e.g., dipped in a reservoir of cauterizing agent, swabbed with cauterizing agent, etc.) and the coated treatment element applicator may be applied to tissue to be treated. In some embodiments, the treatment element may be configured to apply cauterizing agent to the patient over a prolonged period of time (e.g., 30 seconds, 1 minute, 2 minutes, etc.). In some embodiments, the treatment element 232 includes shields configured to protect tissue surrounding the tissue to be treated from coming into contact with the cauterizing agent. In some embodiments, a separate element is used to shield tissue surrounding the tissue to be treated from coming into contact with the cauterizing agent. While such treatments may be performed without the application of energy, in some embodiments, they are performed in conjunction with energy treatments.

In some embodiments, a treatment element may be configured to treat tissue by applying treatment (e.g., energy, cryotherapy, or other treatments) from a position external to the patient's spine. For example, in some embodiments, the devices may be configured to apply energy from an element positioned outside a patient's body, such as on the skin.

In some embodiments, the device is configured to position tissue to be re-shaped. In some embodiments, the device includes features or mechanisms to pull, push or position the intervertebral disc tissue into a mold for re-shaping. For example, suction, counter traction, or compression between two parts of the device may be used.

In some embodiments, the treatment device includes one or more molds configured to re-shape tissue. The mold or re-shaping element may be fixed in size or may vary in size. The mold may also be fixed in shape or may vary in shape. For example, the size or shape of the element may be varied or adjusted to better conform to the disc of a patient. Adjustability may be accomplished using a variety of means, including, for example, mechanically moving the mold by way of joints, arms, guidewires, balloons, screws, stents, or scissoring arms, among other means. The mold may be adjusted manually or automatically.

In some embodiments, the mold or re-shaping element includes a separate or integrated energy-delivery or treatment element (e.g., an electrode). The treatment element may be fixed or adjustable in size. For example, the treatment element may be adjusted to better conform to the intervertebral disc of a patient. In the case of a separate re-shaping element and treatment element, a distance between the two elements may either be fixed or adjustable. Adjustability may be accomplished using a variety of means, including, for example, mechanically moving the mold by way of joints, arms, guidewires, balloons, screws, stents, or scissoring arms, among other means.

In some embodiments, the mold or another part of the device is configured to deliver cooling (discussed in more detail below). In some embodiments, the mold or re-shaping element includes a balloon configured to reshape and/or deform tissue. A balloon may also be configured to deliver energy-based treatment using liquid or gas that is heated or cooled.

Various electrode arrangements may be used for applying energy to the tissue. These electrodes may, for example, deliver RF energy to preferentially shape the tissue to ameliorate symptoms of a herniated or bulging disc. In some embodiments, one or more electrodes may be used alone or in combination with a tissue shaping device or mold. In other embodiments, one or more electrodes may be integrally formed with a tissue shaping device or mold so that the electrodes themselves create the shape for the tissue. In some embodiments, the energy-delivery devices may use alternating current. In some embodiments, the energy-delivery devices may use direct current. In certain such embodiments, the energy-delivery device may include a configuration that uses a grounding pad.

In some embodiments, the term "electrode" refers to any conductive or semi-conductive element that may be used to treat the tissue. This includes, but is not limited to metallic plates, needles, and various intermediate shapes such as dimpled plates, rods, domed plates, and other configurations. Electrodes may also be configured to provide tissue deformation in addition to energy-delivery. Unless specified otherwise, electrodes described can be monopolar (e.g., used in conjunction with a grounding pad) or bipolar (e.g., alternate polarities within the electrode body or used in conjunction with other tissue-applied electrodes).

In some embodiments, the treatment element 232 may include a substantially cylindrical central portion with an end-cap section that is semi-spherical, semi-ellipsoid, or another shape. The end-cap section can be located at proximal or distal ends of the treatment element 232. In alternative embodiments, the treatment element may include a substantially ellipsoid shape In some embodiments, the treatment element 232 may include a clamp, such as to attach to a portion of a treatment site (e.g., as shown in FIG. 3).

Figure 3:
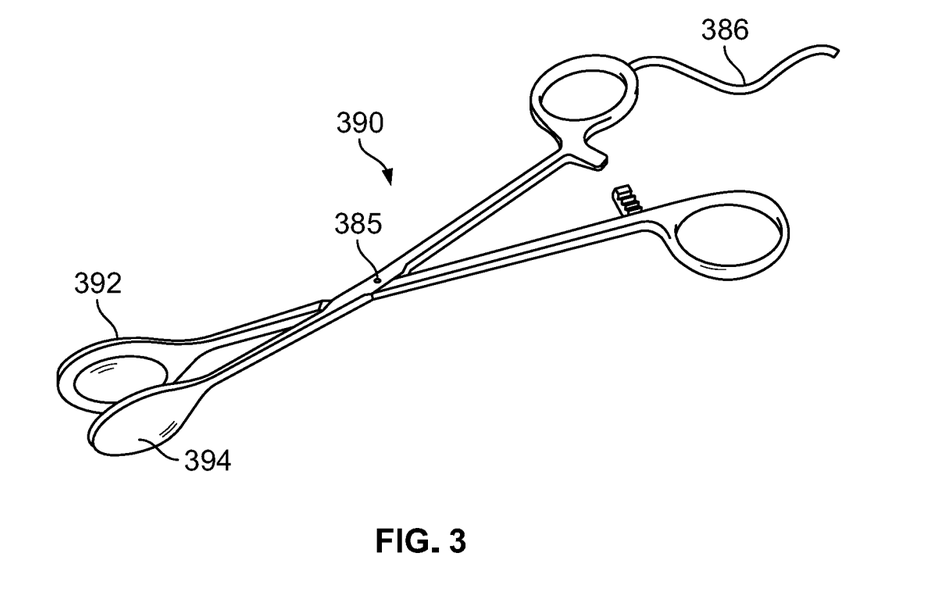
FIG. 3 illustrates an example clamp treatment device.

FIG. 3 illustrates an example clamp treatment device 390. The treatment device 390 is structured as a clamp device configured to engage a targeted section of a treatment site with either a clamping force or a spreading force. In some embodiments, the treatment device 390 may include energy-delivery elements (of any type described herein) which may be powered by a fluid lumen or cable 386. The treatment device 390 includes a first clamp member 392 and a second clamp member 394 joined at a hinge point 385. The clamp members 392, 394 may be configured to attach to a treatment site. In some embodiments, the clamp members 392, 394 may able to be locked in position relative to each other. In the illustrated embodiment, the first clamp member 392 includes an energy-based treatment element (e.g., applying energy to or removing energy from a treatment site). In some embodiments, the tissue-engaging tips may be removable to allow for sterilization and/or to allow for tips of a wide range of shapes and sizes to be used with a single clamp handle.

Figure 4:
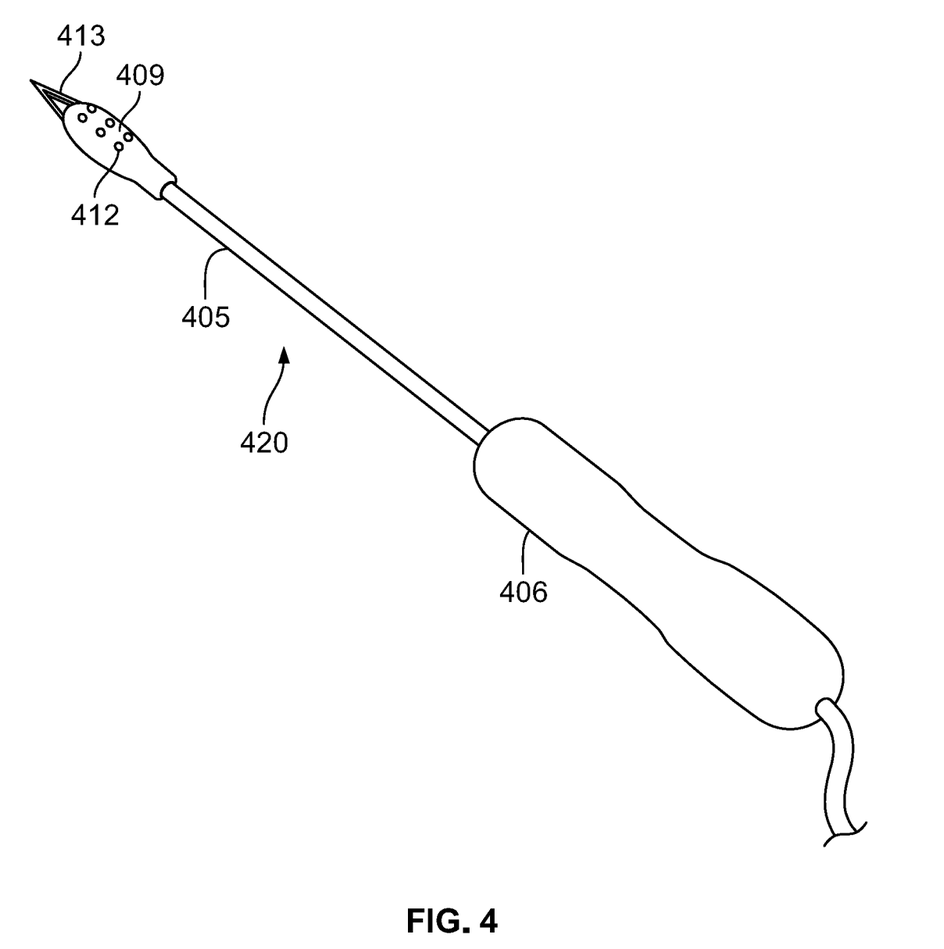
FIG. 4 illustrates an example treatment device for creating an incision in surface tissue (e.g., skin) and treating a treatment site.

FIG. 4 illustrates an example treatment device 420 for creating an incision in surface tissue (e.g., skin) and treating a treatment site. The device 420 may include a handle 406 having a shaft 405 extending therefrom. At an end of the shaft 405 opposite the handle 406, the device 420 may further include a head portion 409. The device 420 may include a blade 413 for creating an incision. In some embodiments, the blade 413 may be removable and/or retractable. The blade 413 may create an incision directly over a target tissue or may create an incision offset from the target tissue. When the incision is offset from the target tissue, the blade 413 may be used to dissect a path from the incision to the target tissue to contact the target tissue with an electrode array 412 of the head portion 409 of the device 420. When the electrode array 412 contacts the target tissue, the device 420 may be used to apply energy through the electrode array 412 to the target tissue.

In alternative embodiments, the blade 413 may be replaced by one or more other suitable cutting members, such as a cutting electrode that may cauterize tissue. As mentioned above, other incision-based treatment devices may include no cutting member, and whatever incision is used for a procedure may be formed with a separate cutting device.

Figure 5:
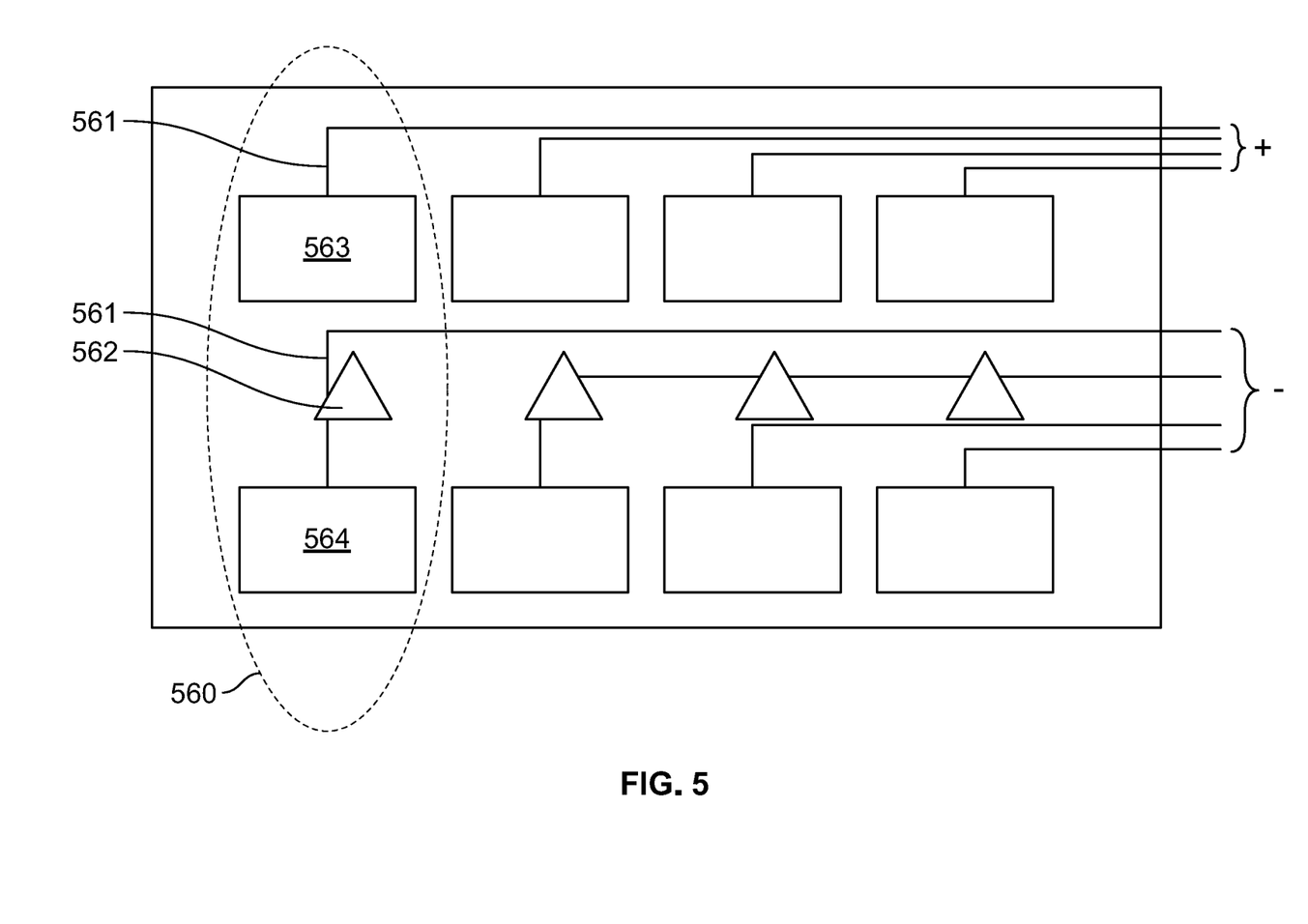
FIG. 5 is a block diagram depicting an array of electrodes of a treatment device arranged in a multi-channel configuration.

FIG. 5 is a block diagram depicting an array of electrodes of a treatment device arranged in a multi-channel configuration. Different treatment sites may have treatment surface areas of varying size and shape. Additionally, clinicians operating a treatment device may vary in skill, dexterity, and habits. Due to these variabilities, each electrode pair of the device may have varying degrees of contact with tissue of the treatment site. For a configuration in which all pairs of electrodes are controlled by one main electrical channel, this may lead to varying magnitudes of treatment energy passing through each electrode pair. The pair(s) of electrodes that have a higher degree of contract with the tissue may experience higher magnitudes of impedance in their individual circuit. Since treatment energy takes the path of least resistance, this may lead to treatment energy being diverted to pairs of electrodes that experience a relatively lower magnitude of impedance due to a relatively lower degree of tissue contact. Thus, it may be advantageous to control the treatment energy through each electrode to ensure repeatable treatments.

In some embodiments, each pair of electrodes may have a separate, controlled electrical channel to allow for different regions of the treatment element to be activated separately. In some embodiments, each electrode pair may be paired with its own thermocouple. By controlling the treatment energy flowing through each pair of electrodes using parameters including, but not limited to, temperature, a greater degree of control and accuracy over the treatment energy may be obtained, such that treatments may be repeatable.

As shown in FIG. 5, the treatment device may include one or more thermocouples 562 and an RF output channel 561 assigned to each electrode pair for feedback. An electrode pair may include a positive electrode 563 and a negative electrode 564. In some embodiments, the positive electrode 563 and the negative electrode 564 may be positioned opposite to one another. Each electrode pair may have its own individual subsystem 560. The individual subsystem 560 may include a controlled RF output channel 561 and a thermocouple 562 to allow for independent adjustments. The thermocouple 562 may act as a feedback control to ensure that proper temperature is maintained at the treatment site.

Figure 6:
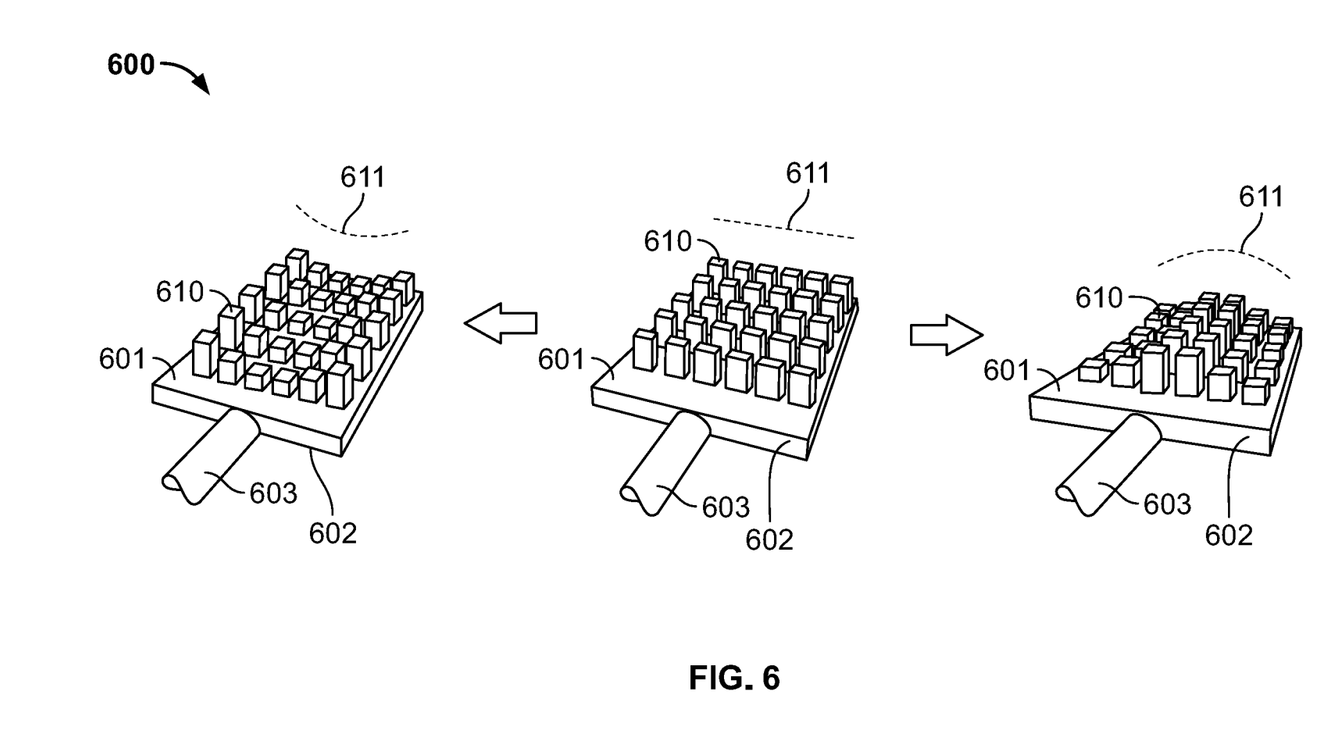
FIG. 6 illustrates an example treatment device having an electrode array.

FIG. 6 illustrates an embodiment of a treatment device 600 including an electrode array 610. The electrode array 610 may include numerous electrodes positioned on a treatment surface 601 of a treatment element 602, which is attached to a shaft 603 of the device 600. In some embodiments, the electrodes may be arranged in a grid pattern. The electrodes may be arranged in any pattern. One or more of the electrodes may be extended or retracted to a preset height. It may be advantageous to manipulate the heights of the electrodes of the electrode array 610 to achieve a combination that forms a required treatment surface profile 611. The treatment surface profile 611 may include any combination of electrode numbers and heights. For example, the electrodes may be arranged and manipulated to achieve a generally concave treatment surface profile, a generally convex treatment surface profile, and/or a generally flat treatment surface profile.

Figure 7:
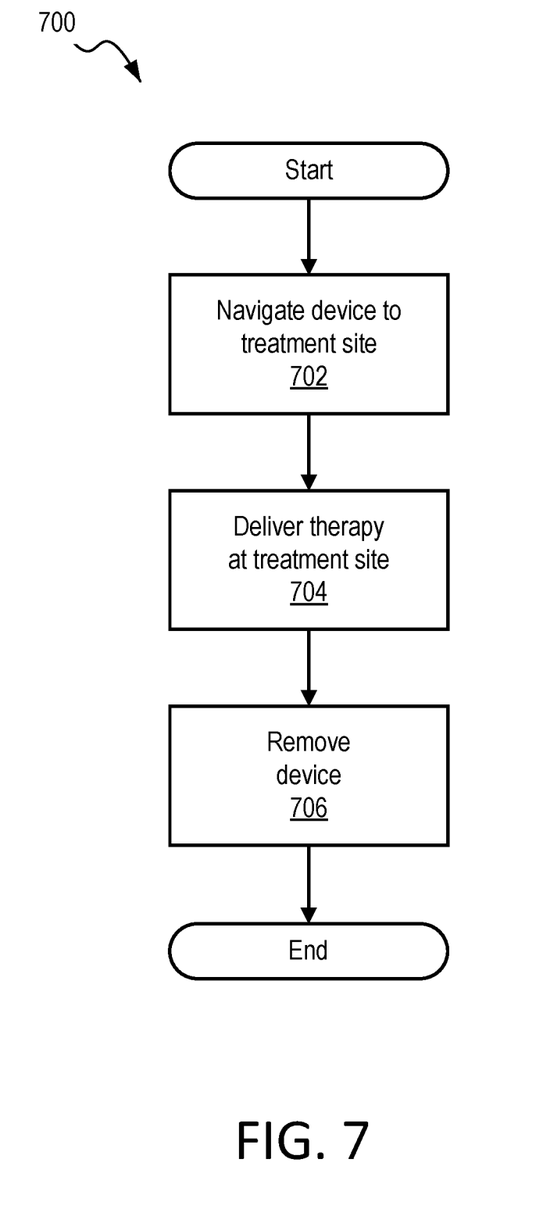
FIG. 7 illustrates an example process for treating tissue.

FIG. 7 illustrates an example process 700 for treating tissue. In certain implementations, the process may include step 702, which recites "navigate device to treatment site". Step 702 may be followed by step 704, which recites "deliver therapy at treatment site". Step 704 may be followed by step 706, which recites "remove device".

In certain implementations, the process 700 may begin with selecting a patient. For example, a clinician can select a patient having symptoms of a spinal condition. In another example, the clinician can select a patient having or thought to be having a condition of the spinal column, such as a bulging or herniated disc.

The process 700 can further include preparing the device. Preparing the device may include removing the device from sterile packaging, assembling one or more components of the device, sterilizing the device, attaching the device to an energy source, and/or other preparatory work. In certain implementations, this step may include customizing the device to suit the particular needs of the patient and the clinician. This may include articulating, manipulating, or otherwise changing one or more components of the device. For example, a clinician may articulate or bend a shaft and/or the treatment portion to place the device in a first, desired configuration. The first, desired configuration may be selected to facilitate navigation of the anatomy of the particular patient to reach the desired treatment site.

In certain circumstances, preparing the device may follow a previous use or a previous attempted use of the treatment device to treat the same or a different treatment site. For example, the clinician may determine that the device is not suitable in its current state, remove the device, and then reconfigure the device in a more suitable format (e.g. a second configuration).

At step 702, the treatment device is navigated to a treatment site. For example, the clinician may navigate the patient's anatomy with the device in the first configuration. Specifically, the clinician may advance a treatment portion of the treatment device into an incision in the patient's back to reach a target treatment site at an intervertebral disc. The goal of the navigation may be to place the treatment element in contact with the treatment site.

In certain circumstances, advancing a portion of the device to a treatment site may follow the removal of the treatment device. In this circumstance, this step may include the clinician wholly or partially re-navigating the device to improve, for example, contact between the treatment portion and the treatment site.

During navigation, the clinician may perform one or more tests to determine whether proper contact with the treatment site has been made. For example, the clinician may activate one or more pairs of the electrodes. Based on measured results, the clinician may determine that proper contact has not been achieved because an energy pathway could not be made between one or more pairs of electrodes and/or that one or more measured electrical parameters (e.g., impedance, voltage, current, etc.) is outside of a desired range. As another example, the clinician may attempt to apply pressure to the treatment site with the treatment portion and determine by feel whether proper contact has been made. As yet another example, the clinician may take a reading using a thermocouple to determine whether proper contact has been made.

Based on the one or more tests, the clinician may determine that proper contact has been made between the treatment portion and the treatment site. In this situation, the flow may move to the step 704, which involves delivering therapy to the treatment site. In certain circumstances, the clinician may determine that proper contact has not been made or that the device is otherwise unsuitable in its current state and the clinician may reposition the device or modify a component thereof and renavigate until proper contact is made.

At step 704, therapy is delivered at the treatment site. In this step, the clinician may cause the device to apply energy to or remove energy from the treatment site. For example, in certain implementations, a clinician may use the device to apply energy to the annulus fibrosus or nucleus pulposus of the intervertebral disc. In some examples, it may be desirable to press the treatment portion against the tissue of the annulus fibrosus or the nucleus pulposus such that the tissue substantially conforms to the shape of the treatment element.

For instance, a concave shape may be formed or the tissue may be otherwise remodeled. In some examples, electrodes of the device may be non-penetrating (e.g., resist penetrating tissue, such as by having a blunt or rounded tip) electrodes that protrude from the treatment surface. The electrodes may create indentations within the tissue without piercing or otherwise penetrating into the tissue. A portion of the tissue may enter and conform to the shape of a trough of the treatment device and contact a thermocouple. While the tissue is in this configuration, the clinician may activate one or more pairs of electrodes of the treatment device to deliver therapy to the treatment site. In certain implementations, delivering therapy to the treatment site may include delivering radio frequency energy from a first electrode on the treatment portion to a second electrode on the treatment portion to treat tissue selected from the group of the annulus fibrosus, nucleus pulposus, bone, muscle, skin or other tissue to modify a property of the at least one tissue and thus treat a bulging disc or other condition of the vertebral column. The modification can remain after the treatment element is removed and the tissue heals or otherwise recovers from the treatment.

At step 706, the device may be removed. In certain circumstances, the clinician may remove part or all of the device from the patient. The clinician may determine that one or more further adjustments may improve contact between the treatment portion and the treatment site or otherwise achieve improved therapeutic results. In such circumstances, the flow may move back to the start, and the clinician may re-prepare the device or the patient for treatment. For example, the clinician may articulate one or more components of the device to place the device in a second configuration. The clinician may then navigate to a new or the same treatment site and deliver therapy to the treatment site.

Figure 8A:
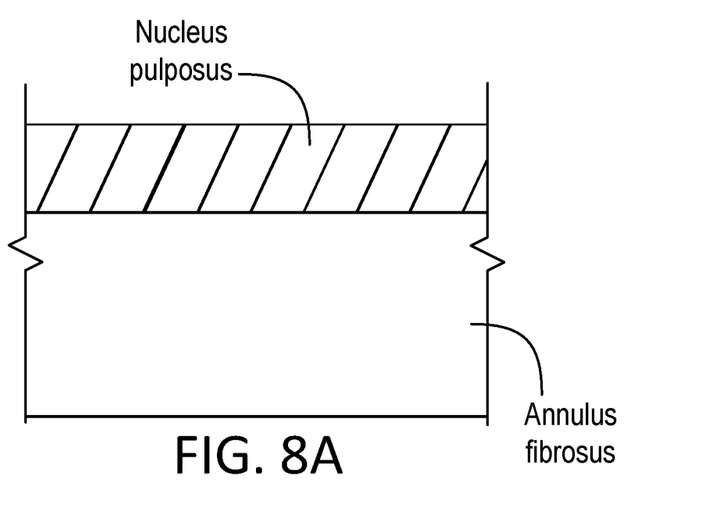
FIG. 8A illustrates an example cross-section of tissue at an intervertebral disc.
Figure 8B:
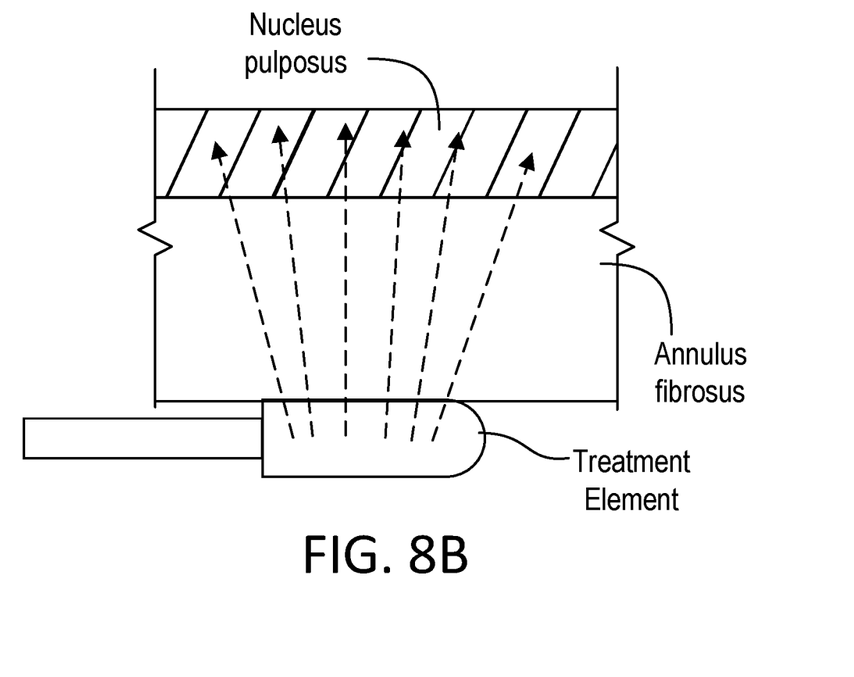
FIG. 8B illustrates treatment of tissue of the intervertebral disc with a treatment element.

FIG. 8A shows a cross-section of tissue at an intervertebral disc. The cross-section shows nucleus pulposus beneath a layer of annulus fibrosus. FIG. 8B illustrates treatment of the tissue of the intervertebral disc with a treatment element. When the treatment element is activated, both the nucleus pulposus and the annulus fibrosus are affected by the treatment produced by the energy-based treatment element. For example, they can be heated by current flowing from an electrode of the treatment element to a return electrode (e.g., a grounding pad). In another example, the tissue can be heated by current flowing from a first electrode to a second electrode of the treatment element. In yet another example, the tissue can be cooled by the treatment element delivering cryotherapy. The tissue closest to the treatment element receives the highest treatment amount (e.g., the highest current density, and thus, the highest heat). In examples where the treatment element includes a heating element (e.g., one or more RF electrodes), a surface cooling mechanism may allow the temperature of the treatment surface to be reduced. Such a cooling mechanism may maintain a lower temperature at the annulus fibrosus even though current flow will continue to heat the nucleus pulposus. The treatment can cause a modification of the properties of some or all of the treated tissue.

Figure 9:
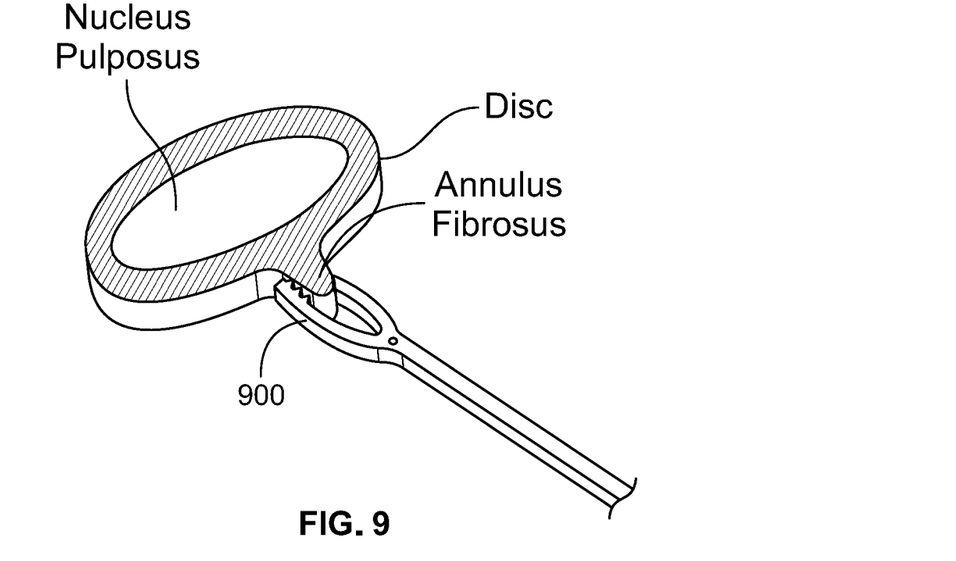
FIG. 9 illustrates an example treatment of an intervertebral disc using a clamp treatment element.

FIG. 9 illustrates an example treatment of an intervertebral disc using a clamp treatment element 900. As illustrated, a clamp portion of the treatment element 900 is closed around a portion of the annulus fibrosus. This can help direct treatment to a portion of the annulus fibrosus within the clamp. For example, energy-based treatment can be applied to the tissue. In some examples, treatment can be applied to shrink or otherwise modify the annulus fibrosus or the nucleus pulposus to treat the disc.

Figure 10:
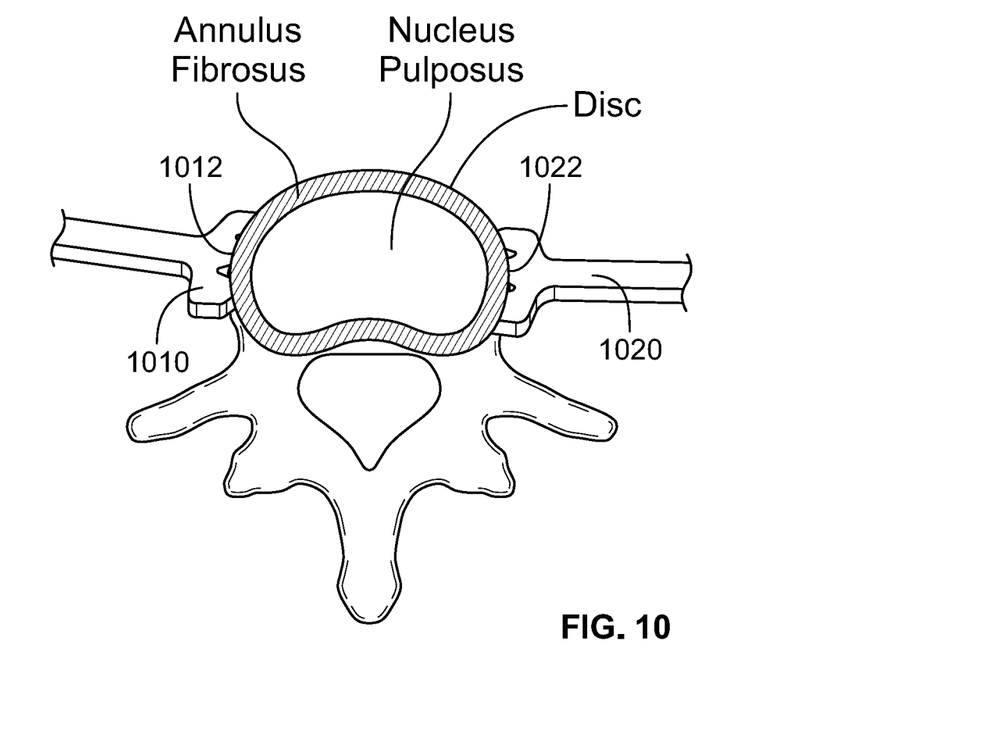
FIG. 10 illustrates an example treatment of an intervertebral disc using two treatment elements.

FIG. 10 illustrates an example treatment of an intervertebral disc using a first treatment element 1010 and a second treatment element 1020. The placement of the treatment elements 1010, 1020 can direct treatment through the disc.

For example, where the treatment is a radio frequency-based treatment, radio frequency energy can be directed from an electrode 1012 of the first treatment element 1010 to an electrode 1022 of the second treatment element 1020. The electrode 1012 of the first treatment element 1010 can be placed in a first location (e.g., a location near the disc bulge) and the electrode 1022 of the second treatment element 1020 can be placed in a second location (e.g., on a contralateral side of the disc) to help direct energy-based treatment through the area of the disc to shrink or otherwise modify the tissue of the disc (e.g., a bulging portion of the disc).

Figure 11:
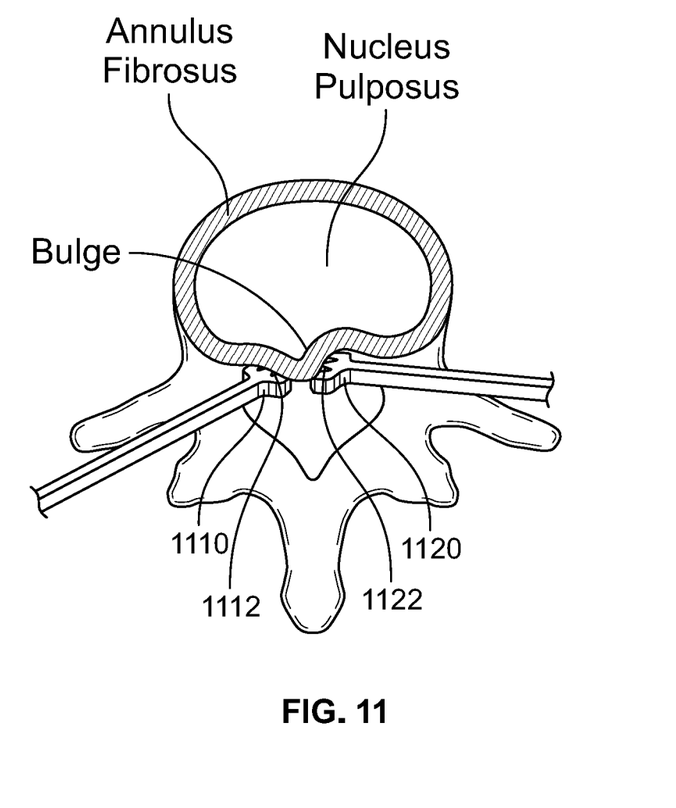
FIG. 11 illustrates an example treatment of an intervertebral disc using two treatment elements.

FIG. 11 illustrates an example treatment of an intervertebral disc using a first treatment element 1110 and a second treatment element 1120. The treatment elements 1110, 1120 are positioned near a bulge in the disc. Energy can be applied to or removed from the disc using the treatment elements 1110, 1120 to shrink or otherwise modify the tissue of the bulge. For example, where RF treatment is used, RF energy can flow from an electrode 1112 of the first treatment element 1110 through the bulge to an electrode 1122 of the second treatment element 1120, thereby creating a modification in the bulge.

Although various embodiments are described herein, the present invention extends beyond the specifically disclosed embodiments to other alternative embodiments and/or uses of the invention and modifications and equivalents thereof. Thus, the scope of the present invention should not be limited by the disclosed embodiments, but should be determined only by a fair reading of the claims that follow.

What is claimed is:

1. A method of treating an intervertebral disc in a patient, without piercing the disc, the method comprising:
   navigating a treatment element of an energy delivery device to a bulge in the intervertebral disc;
   pressing a treatment surface of the treatment element against an exterior of the bulge in the intervertebral disc, so that the bulge conforms to a shape of the treatment surface, wherein the treatment surface comprises two rows of bipolar radiofrequency electrodes, and wherein the exterior of the bulge comprises annulus fibrosis or nucleus pulposus of the intervertebral disc;
   applying radiofrequency energy from a first row of the two rows of bipolar radiofrequency electrodes to a second row of the two rows, so that the radiofrequency energy passes through the exterior of the bulge to shrink at least one of the annulus fibrosis or the nucleus pulposus and thus shrink the bulge; and
   removing the treatment element from the patient,
   wherein the bulge in the intervertebral disc remains shrunken after the treatment element is removed, thereby treating the intervertebral disc.

2. The method of claim 1, further comprising measuring a temperature of at least one of the annulus fibrosis or the nucleus pulposus with a temperature sensing member on the treatment surface.

3. The method of claim 2, further comprising adjusting an amount of the radiofrequency energy applied to the annulus fibrosis or the nucleus pulposus, based at least in part on the measured temperature.

4. The method of claim 1, further comprising:
   activating one or more pairs of the bipolar radiofrequency electrodes; and
   determining that proper contact has been made between the treatment surface and the exterior of the bulge before applying the radiofrequency energy.

5. The method of claim 1, further comprising cooling the exterior of the bulge of the intervertebral disc at least one of before, during, or after applying the radiofrequency energy.

6. A method of treating an intervertebral disc in a patient, without piercing the disc, the method comprising:
   navigating a first treatment element of a first bipolar radiofrequency energy delivery device to a bulge in the intervertebral disc;
   contacting the first treatment element with a first treatment site on an exterior of the bulge in the intervertebral disc, wherein the exterior of the bulge comprises annulus fibrosis or nucleus pulposus of the intervertebral disc;
   navigating a second treatment element of a second bipolar radiofrequency energy delivery device to the bulge in the intervertebral disc;
   contacting the second treatment element with a second treatment site on the exterior of the bulge in the intervertebral disc;
   applying radiofrequency energy through the exterior of the bulge in the intervertebral disc using the first and second treatment elements to shrink at least one of the annulus fibrosis or the nucleus pulposus and thus shrink the bulge, thereby treating the intervertebral disc; and
   removing the first and second treatment elements from the patient;
   wherein the bulge in the intervertebral disc remains shrunken after the first and second treatment elements are removed.

7. The method of claim 6, wherein applying the radiofrequency energy comprises transmitting energy from the first treatment element to the second treatment element.

8. The method of claim 6, further comprising cooling tissue of the intervertebral disc before, during, or after applying the radiofrequency energy.

9. The method of claim 6, wherein the first treatment site and the second treatment site are on opposite sides of the bulge in the intervertebral disc.

* * * * *